United States Patent
Govari et al.

(10) Patent No.: US 12,402,937 B2
(45) Date of Patent: Sep. 2, 2025

(54) INITIATING IRE GENERATION WITH A RAMP

(71) Applicant: BIOSENSE WEBSTER (ISRAEL) LTD., Yokneam (IL)

(72) Inventors: Assaf Govari, Haifa (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 742 days.

(21) Appl. No.: 17/672,823

(22) Filed: Feb. 16, 2022

(65) Prior Publication Data
US 2022/0287764 A1 Sep. 15, 2022

Related U.S. Application Data

(60) Provisional application No. 63/159,412, filed on Mar. 10, 2021.

(51) Int. Cl.
| | |
|---|---|
| A61B 18/00 | (2006.01) |
| A61B 18/14 | (2006.01) |
| A61B 18/16 | (2006.01) |
| A61B 18/12 | (2006.01) |

(52) U.S. Cl.
CPC .......... *A61B 18/1485* (2013.01); *A61B 18/16* (2013.01); *A61B 2018/00577* (2013.01); *A61B 2018/00613* (2013.01); *A61B 2018/00821* (2013.01); *A61B 2018/00839* (2013.01); *A61B 2018/126* (2013.01); *A61B 2018/167* (2013.01)

(58) Field of Classification Search
None
See application file for complete search history.

(56) References Cited

U.S. PATENT DOCUMENTS

| | | | |
|---|---|---|---|
| 5,391,199 A | 2/1995 | Ben-Haim | |
| 6,107,699 A * | 8/2000 | Swanson | A61B 18/1492 307/115 |
| 6,239,724 B1 | 5/2001 | Doron | |

(Continued)

FOREIGN PATENT DOCUMENTS

| | | |
|---|---|---|
| WO | WO96/05768 | 2/1996 |
| WO | 2012088149 A2 | 6/2012 |

OTHER PUBLICATIONS

Extended European Search Report, received for European Application No. 22160986.0, mailed on Jul. 27, 2022, 7 pages.

*Primary Examiner* — Linda C Dvorak
*Assistant Examiner* — Nicholas S Borsch

(57) ABSTRACT

A method for ablating tissue in a subject, including providing a probe, having an electrode, that is inserted into a lumen of the subject, so that the electrode is in proximity to the tissue to be ablated. An immobilizing signal is injected into the subject, via the electrode, that immobilizes the subject. When the subject is immobilized, an ablation signal is injected via the electrode into the subject, the ablation signal being configured to ablate the tissue of the subject by irreversible electroporation. The ablation signal has at least one train of first pulses, each of the first pulses in the at least one train having a first pulse absolute amplitude, and the immobilizing signal has one or more trains of second pulses, each of the second pulses in the one or more trains having a second pulse absolute amplitude less than the first pulse absolute amplitude.

18 Claims, 4 Drawing Sheets

(56) References Cited

U.S. PATENT DOCUMENTS

| | | |
|---|---|---|
| 6,332,089 B1 | 12/2001 | Acker |
| 6,484,118 B1 | 11/2002 | Govari |
| 6,618,612 B1 | 9/2003 | Acker |
| 6,690,963 B2 | 2/2004 | Ben-Haim |
| 8,456,182 B2 | 6/2013 | Bar-Tal |
| 9,867,652 B2 | 1/2018 | Sano |
| 10,286,108 B2 | 5/2019 | Davalos |
| 2002/0065455 A1 | 5/2002 | Ben-Haim |
| 2002/0091385 A1* | 7/2002 | Paton ................ A61B 18/1442 606/51 |
| 2003/0120150 A1 | 6/2003 | Govari |
| 2004/0068178 A1 | 4/2004 | Govari |
| 2007/0066957 A1* | 3/2007 | Demarais ........... A61N 1/36007 604/20 |
| 2012/0220999 A1 | 8/2012 | Long |
| 2013/0012938 A1* | 1/2013 | Asirvatham ............ A61N 1/20 606/41 |
| 2018/0289417 A1 | 10/2018 | Schweitzer |
| 2018/0318000 A1* | 11/2018 | Honda ................ A61B 18/1445 |
| 2021/0161592 A1 | 6/2021 | Altmann et al. |

\* cited by examiner

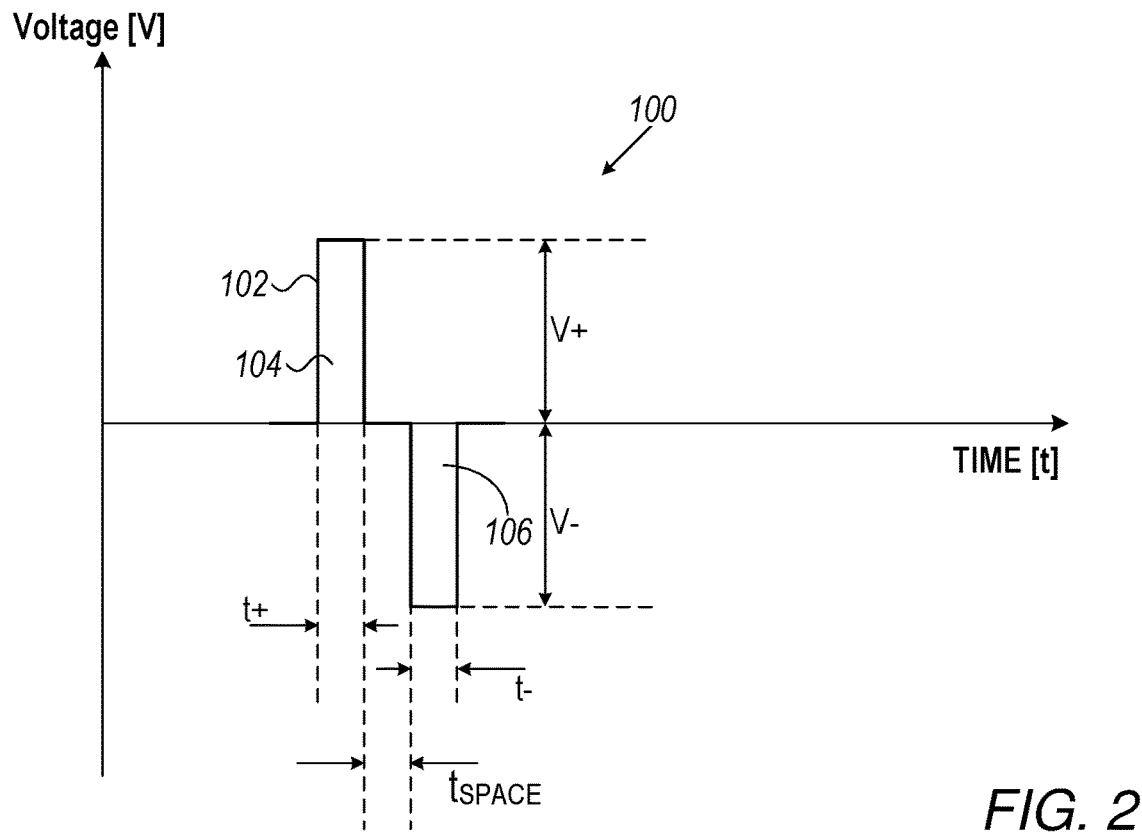
FIG. 2
FIG. 3
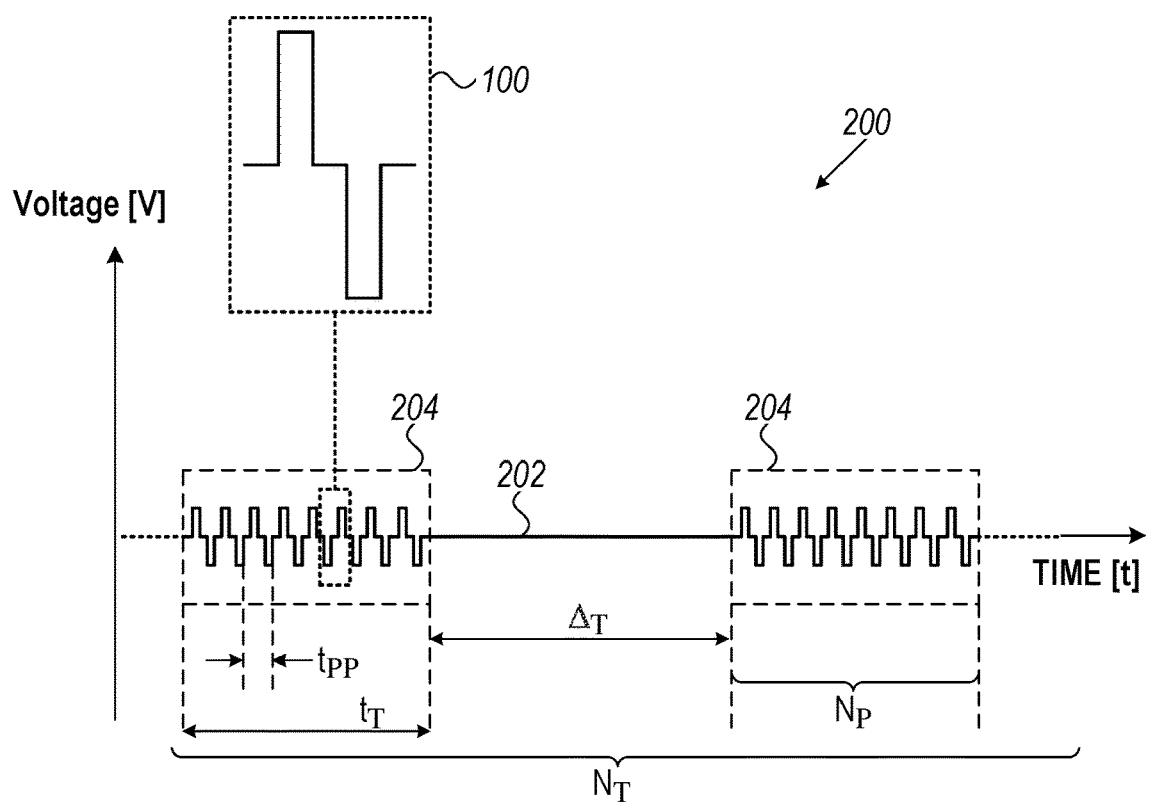

INITIATING IRE GENERATION WITH A RAMP

CROSS-REFERENCE TO RELATED APPLICATION

This application claims the benefit of U.S. Provisional Patent Application 63/159,412, filed 10 Mar. 2021, which is incorporated herein by reference.

FIELD OF THE DISCLOSURE

This disclosure relates generally to ablation used for surgery, and specifically to ablation performed using irreversible electroporation (IRE).

BACKGROUND

IRE is a soft tissue ablation technique that applies short pulses of strong electrical fields to create permanent and hence lethal nanopores in the cell membrane, thus disrupting the cellular homeostasis (internal physical and chemical conditions). Cell death following IRE results from apoptosis (programmed cell death) and not necrosis (cell injury, which results in the destruction of a cell through the action of its own enzymes) as in all other thermal or radiation based ablation techniques. IRE is commonly used in tumor ablation in regions where precision and conservation of the extracellular matrix, blood flow and nerves are of importance. Some examples of systems using IRE are provided below.

U.S. Pat. No. 9,867,652, to Sano et al., describes IRE applied through the vasculature of organs to treat tumors embedded deep within the tissue or organ, or to decellularize organs to produce a scaffold from existing animal tissue with the existing vasculature intact. The patent states that "By gradually increasing voltage and testing cells in a given tissue, one can determine a point where irreversible electroporation occurs."

U.S. Patent Application 20180289417 A1 to Schweitzer et al., describes electroporation systems and methods of preconditioning tissue for electroporation therapy. An electroporation generator includes an electroporation circuit and a preconditioning circuit. The preconditioning circuit is configured to be coupled to a preconditioning electrode for stimulating skeletal muscle tissue of the patient, and is further configured to transmit a preconditioning signal to a preconditioning electrode.

U.S. Pat. No. 10,286,108 to Davalos, describes how IRE may be used to create tissue scaffolds. Scaffolds are derived from natural tissues and are created using non-thermal irreversible electroporation.

The present disclosure will be more fully understood from the following detailed description of the examples thereof, taken together with the drawings, in which:

BRIEF DESCRIPTION OF THE DRAWINGS

FIG. 2 is a schematic voltage vs. time graph of a bipolar IRE pulse;

FIG. 3 is a schematic voltage vs. time graph of a burst of bipolar pulses;

DESCRIPTION OF EXAMPLES

Overview

A basic problem with applying IRE ablation is that when an IRE pulse is initially applied to a subject, the subject may jump or spasm. The spasm is caused by the high electrical fields of the high voltage IRE pulse creating a skeletal or phrenic contraction of the subject muscles. The spasm may lead to a traumatic situation, for example if a catheter probe has been initially positioned at a desired location in the myocardium.

Rather than initially applying the IRE pulses at their full voltage amplitude, examples of the present disclosure incorporate a ramp period into the pulse generation. During the ramp period, the amplitudes of the pulses are gradually increased while being kept less than an effective IRE voltage. During the ramp period, the amplitudes of the pulses are low enough so that IRE does not occur. After the ramp period the full IRE voltage amplitude may be applied, so that IRE does occur.

The initial low voltage pulses lock the subject muscles without causing IRE, so that the subject is immobilized and there is no spasm when the full IRE voltage is achieved.

The ramp may be any convenient shape, such as linear or exponential. A typical length for the ramp period is approximately 0.5 s.

System Description

Figure 1:
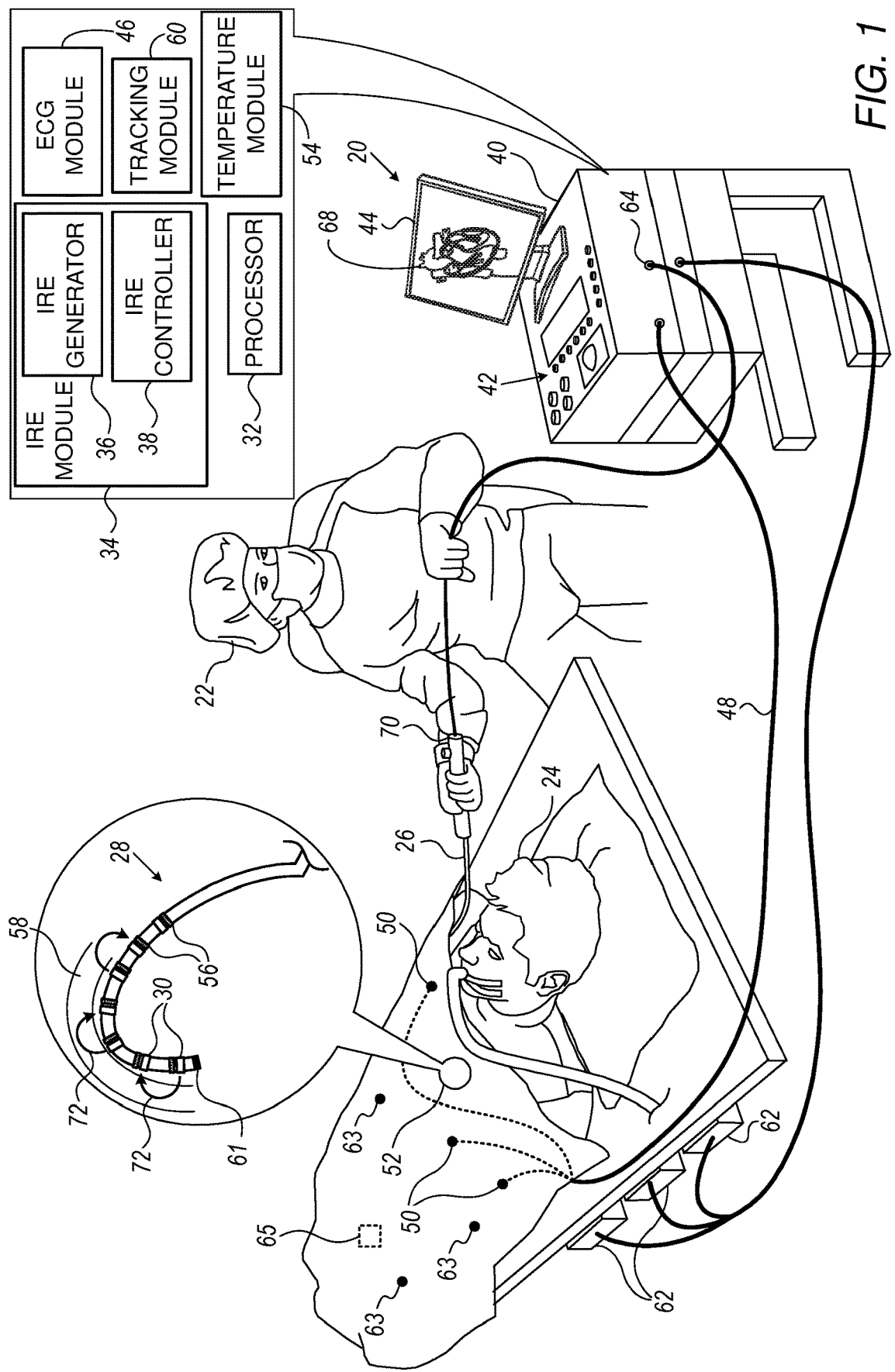
FIG. 1 is a schematic illustration of an IRE (irreversible electroporation) system used for an ablation procedure.

Reference is now made to FIG. 1, which is a schematic pictorial illustration of a multi-channel IRE (irreversible electroporation) system 20 used in an IRE ablation procedure. In the pictured example, a physician 22 performs a multi-channel IRE ablation procedure using IRE system 20. Physician 22 performs the procedure on a heart 52 of a subject 24, using an ablation catheter probe 26 having a distal end 28 comprising multiple ablation electrodes 30 arranged along the length of the distal end.

IRE system 20 comprises a processor 32 and an IRE module 34, and the IRE module comprises an IRE generator 36 and an IRE controller 38. An IRE generator similar to generator 36 is described in U.S. patent application Ser. No. 16/701,989. As is detailed below, IRE generator 36 generates trains of electrical pulses, which are directed to selected electrodes 30 so as to generate currents 72 therebetween, for performing an IRE procedure. The waveforms (timing and amplitude) of the trains of electrical pulses are controlled by IRE controller 38. Processor 32, as is also detailed below, operates the input and output interface between IRE system 20 and physician 22.

Processor 32 and IRE controller 38 each typically comprise a programmable processor, which is programmed in software and/or firmware to carry out the functions that are described herein. Alternatively or additionally, the processors and the controller may comprise hard-wired and/or programmable hardware logic circuits, which perform at least some of these functions. Although processor 32 and IRE controller 38 are shown in the figures, for the sake of simplicity, as separate, monolithic functional blocks, in practice some of these functions may be combined in a single processing and control unit. In some examples, IRE controller 38 resides within IRE module 34, since typically high-speed control signals are transmitted from the IRE controller to IRE generator 36. However, provided that signals at sufficiently high speeds may be transmitted from processor 32 to IRE generator 36, IRE controller 38 may reside within the processor.

Processor 32 and IRE module 34 typically reside within a console 40. Console 40 comprises input devices 42, such as a keyboard and a mouse, operated by physician 22. A display screen 44 is located in proximity to console 40. Display screen 44 may optionally comprise a touch screen, thus providing another input device.

IRE system 20 may additionally comprise one or more of the following modules (typically residing within console 40):

An electrocardiogram (ECG) module 46 is coupled through a cable 48 to ECG electrodes 50, which are attached to subject 24. ECG module 46 is configured to measure the electrical activity of heart 52 of subject 24.

A temperature module 54 is coupled to temperature sensors 56, such as thermocouples, located adjacent to each electrode 30 on distal end 28 of catheter 26, and is configured to measure the temperature of adjacent tissue 58.

A tracking module 60 is coupled to one or more electromagnetic position sensors 61 in distal end 28. In the presence of an external magnetic field generated by magnetic-field generators 62, the electromagnetic position sensors output signals that vary with the positions of the sensors. Based on these signals, tracking module 60 may ascertain the positions of electrodes 30 in heart 52.

A method of position tracking using external magnetic fields is implemented in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1.

Alternatively or additionally, module 60 may use a tracking system based on currents transferred through, or impedances seen by, electrodes 30. In such a system module 60 estimates the position of a given electrode 30 in response to currents or impedances between the given electrode and a plurality of surface-electrodes 63 that are coupled to the skin of subject 24. An Advanced Current Location (ACL) system, made by Biosense-Webster (Irvine, California), which is described in U.S. Pat. No. 8,456,182, is such a tracking system.

Catheter 26 is coupled to console 40 via an electrical interface 64, such as a port or socket. IRE signals are thus carried to distal end 28 via interface 64. Similarly, signals for tracking the position of distal end 28, and/or signals for tracking the temperature of tissue 58, may be received by processor 32 via interface 64 and applied by IRE controller 38 in controlling the pulses generated by IRE generator 36.

An external electrode 65, or "return patch", may be additionally coupled externally between subject 24, typically on the skin of the subject's torso, and IRE generator 36.

The IRE signals generated by the IRE module are described below, with reference to FIGS. 2 and 3 and Table I. Except as stated below, the signals generated by the module are used by selected electrodes 30 to ablate tissue 58 that is in proximity to the electrodes.

FIG. 2 is a schematic illustration of a voltage vs. time graph of a bipolar IRE pulse 100, according to an example of the present disclosure.

A graph 102 depicts the voltage V of bipolar IRE pulse 100 as a function of time t. The bipolar IRE pulse comprises a positive pulse 104 and a negative pulse 106, where the terms "positive" and "negative" refer to an arbitrarily chosen polarity of two selected electrodes 30 between which the bipolar pulse is applied. The amplitude of positive pulse 104 is labeled as V+, and the temporal width of the pulse is labeled as t+. Similarly, the amplitude of negative pulse 106 is labeled as V−, and the temporal width of the pulse is labeled as t−. The time between positive pulse 104 and negative pulse 106 is labeled as $t_{SPACE}$. Typical values for the parameters of bipolar pulse 100 are given in Table 1, below.

FIG. 3 is a schematic illustration of a voltage vs. time graph of a burst 200 of bipolar pulses, according to an example of the present disclosure.

In an IRE procedure, the IRE signals are typically conveyed between a selected pair of electrodes 30 as one or more bursts 200, depicted by a graph 202, so that one of the pair may be considered to act as an injection electrode, while the other of the pair acts as a return electrode. Alternatively, the IRE signals may be conveyed between one selected electrode 30 and external electrode 65, in which case selected electrode 30 may be considered to act as an injection electrode while external electrode 65 acts as a return electrode.

Burst 200 comprises $N_T$ pulse trains 204, where each train comprises $N_P$ bipolar pulses 100, and $N_T$, $N_P$ are positive integers. The length of pulse train 204 is labeled as $t_T$. The period of bipolar pulses 100 within a pulse train 204 is labeled as $t_{PP}$, and the interval between consecutive trains is labeled as $\Delta_T$, during which the signals are not applied. Typical values for the signal-defining parameters of the IRE ablation signals of burst 200 are given in Table 1, below.

TABLE I

| Parameter | Symbol | Typical values |
| --- | --- | --- |
| Pulse amplitudes | V+, V− | 500-2000 V |
| Pulse widths | t+, t− | 0.5-5 μs |
| Spacing between positive and negative pulse | $t_{SPACE}$ | 0.1-5 μs |
| Period of bipolar pulses in a pulse train | $t_{PP}$ | 1-20 μs |
| Length of pulse train | $t_T$ | 10 μs-100 μs |
| Number of bipolar pulses in a pulse train | $N_P$ | 1-100 |
| Spacing between consecutive pulse trains | $\Delta_T$ | 0.3-1000 ms |
| Number of pulse trains in a burst | $N_T$ | 1-100 |
| Length of a burst | | 0-500 ms |
| Energy per channel | | ≤200 J |
| Total time for IRE signal delivery | | <10 s |

Immobilizing Signal

As is apparent from FIGS. 2 and 3, and Table I, the IRE signals delivered to subject 24, via one or a pair of selected electrodes 30, comprise high voltage pulses, i.e. pulses having amplitudes up to 2000 V. The inventors have observed that when the IRE signals are initially delivered to the subject, the subject may spasm, and the spasm is believed to be caused by the high voltage/field of the IRE pulses causing skeletal or phrenic contraction of the subject muscles.

The subject's spasm may lead to trauma. The spasm may also lead to movement of electrodes 30 from their initial location, so necessitating repositioning of the electrodes which increases the time of the ablation procedure.

Examples of the present disclosure prevent the subject spasming by injecting an immobilizing signal into subject prior to injecting the IRE ablation signals. The immobilizing signal locks the muscles of the subject, so that the subject no longer spasms when the IRE ablation signals are injected. Typically the immobilizing signal is generally similar to the IRE ablation signals, except that the immobilizing signal has a lower absolute amplitude. The immobilizing signal is described in detail below.

In an example of the present disclosure, the immobilizing signal comprises a set of pulse trains having monotonically increasing amplitudes, all of the amplitudes having absolute values that are less than the absolute values of the amplitudes of the ablating IRE signals. The immobilizing signal is described with reference to FIG. 4 below.

Figure 4:
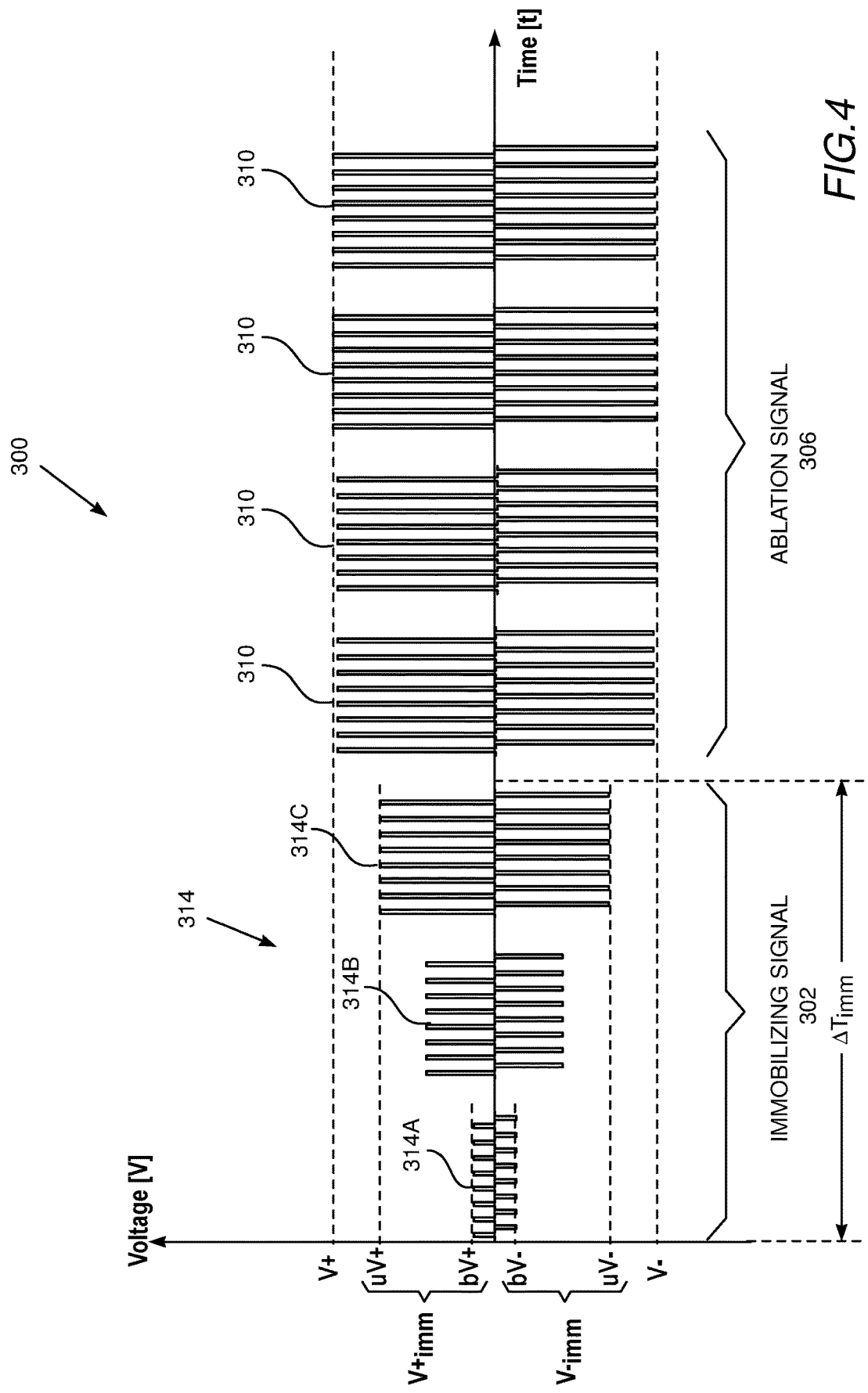
FIG. 4 is a schematic graph of an immobilizing signal and of an IRE ablation signal.

FIG. 4 is a schematic graph 300 of an immobilizing signal and of an IRE ablation signal, according to an example of the present disclosure. Graph 300 is a voltage vs. time graph, and a section 302 of the graph comprises the immobilizing signal, which is also referred to herein as immobilizing signal 302. A section 306 of the graph, comprises the IRE ablation signal, which, as is illustrated, comes temporally after the immobilizing signal. The IRE ablation signal is also referred to herein as IRE ablation signal 306.

The parameters of IRE ablation signal 306 are configured according to Table I. By way of example, signal 306 is assumed to comprise four pulse trains 310, and is also referred to herein as burst 306. The parameters of each pulse train 310, V+, V−, t+, t−, $t_{SPACE}$, $t_{PP}$, $t_T$, $N_P$, are configured to be the same, and are as set forth in Table I. The spacing $\Delta_T$ between consecutive pulse trains 310 is also as set forth in Table I.

Immobilizing signal 302 comprises one or more pulse trains 314A, 314B, 314C, . . . , generically termed pulse trains 314. By way of example, signal 302 is assumed to comprise three pulse trains 314. In an example of the present disclosure, except for pulse amplitudes V+, V−, pulse trains 314 have the same parameters as pulse trains 310. Furthermore, the spacing between pulse trains 314 is the same as for pulse trains 310, and the spacing between a final pulse train of the immobilizing signal and an initial pulse train of the ablation signal is also the same.

As for ablation signal 306, the amplitudes of the pulses within a given pulse train of the immobilizing signal are constant. However, in contrast to ablation signal 306, the amplitudes of the successive pulse trains of immobilizing signal 302, herein termed $V+_{imm}$ and $V-_{imm}$, are not equal to each other, but rather change monotonically with time. I.e., the values of $V+_{imm}$ increase monotonically with time, and the values of $V-_{imm}$ decrease monotonically with time. Thus, the absolute values of the amplitudes of the successive pulse trains of the immobilizing signal increase monotonically in a ramp-like manner.

In a disclosed example, the amplitudes of the immobilizing signal pulse trains change from a lower valued fraction "b" of the amplitudes V+, V− of ablation signal 306 to an upper valued fraction "u" of the amplitudes V+, V−, where $0<b<u<1$. The change may be linear or non-linear, for example exponential. In a disclosed example b=20% and u=70%, but other values of u, b, provided they obey the inequality above, are possible. Typically, and as illustrated in FIG. 4, an overall time, $\Delta T_{imm}$, of immobilizing signal 302 is approximately 0.5 s, but overall times larger or smaller than 0.5 s are possible.

Typical values for the amplitudes of the immobilizing signal pulse trains, and for the overall time of the immobilizing signal, are given in Table II, which lists signal-defining parameters of the immobilizing signal:

TABLE II

| Parameter | Symbol | Typical values |
| --- | --- | --- |
| Immobilizing Signal Pulse amplitudes | $V+_{imm}$ $V-_{imm}$ | Between bV+ and uV+ Between bV− and uV− $0 < b < u < 1$ |
| Overall immobilizing signal time | $\Delta T_{imm}$ | 0.5 s |

Figure 5:
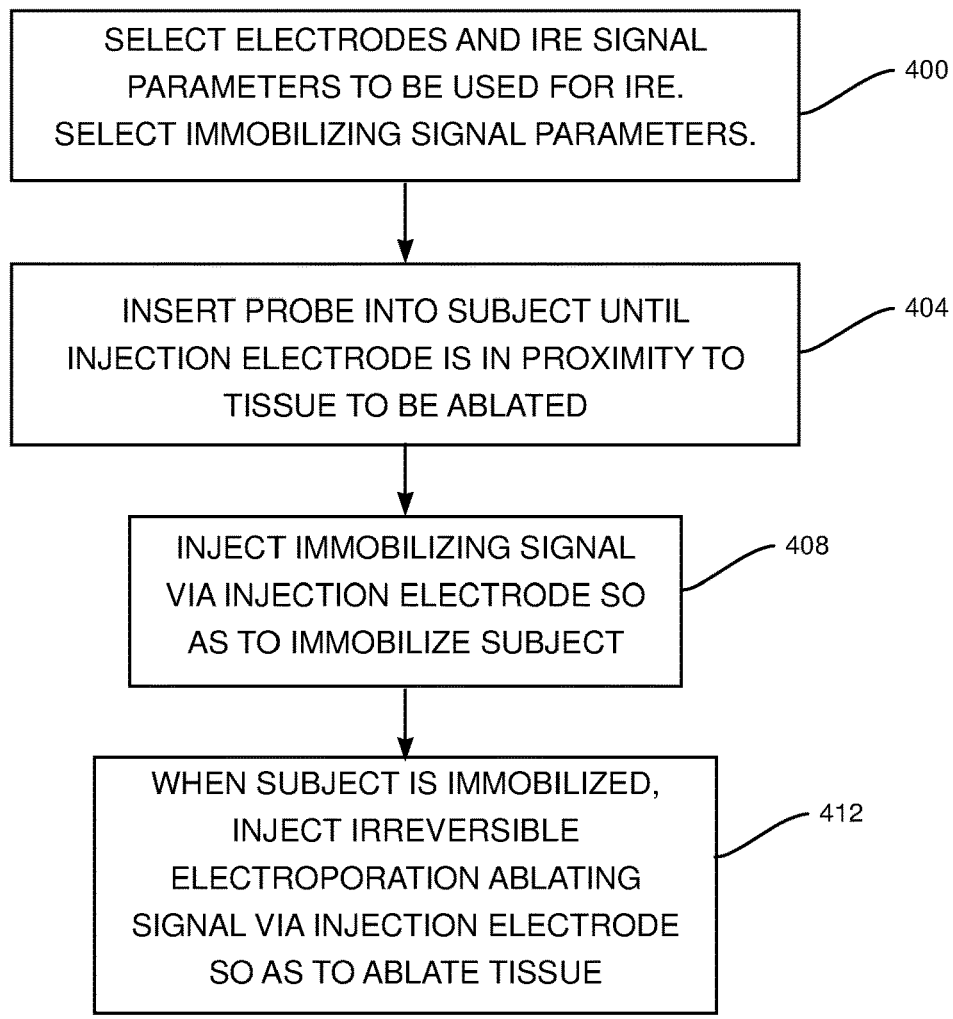
FIG. 5 is a flowchart of steps of an IRE ablation procedure illustrating use of an immobilizing signal.

FIG. 5 is a flowchart of steps of an IRE ablation procedure, illustrating use of an immobilizing signal, according to an example of the present disclosure.

An IRE ablation procedure typically comprises applying multiple bursts 200 of IRE signals between different selected pairs of electrodes 30, and/or between different selected electrodes 30 and external electrode 65. (Each burst is typically applied consecutively to first, second, third, . . . pairs of electrodes.) In examples of the present disclosure immobilizing signal 302 may be applied before each of the bursts; alternatively, immobilizing signal 302 may be applied before selected ones of the bursts; further alternatively, immobilizing signal 302 may be applied before only a first of the bursts.

For simplicity in the following description, the IRE procedure is assumed to comprise one burst 200 that is conveyed between one pair of electrodes, so that one electrode 30 acts as an injection electrode and the other electrode of the pair, which may be an electrode 30 or electrode 65, acts as a return electrode. Those having ordinary skill in the art will be able to modify the description, mutatis mutandis, for the other cases described above, i.e., for multiple bursts 200 applied to more than one pair of electrodes.

In an initial setup step 400, physician 22 selects IRE signal parameters to be used for the procedure. The values are selected as listed in Table I, and as described above with reference to FIGS. 2 and 3. In addition, physician 22 selects values for the immobilizing signal parameters, as listed in Table II and as described above with reference to FIG. 4. The selections may be performed by any convenient method, such as by displaying on screen 44 protocols with preset values of the IRE signal parameters, and of the immobilizing signal parameters, and allowing the physician to choose specific protocols.

In the setup step the physician also selects a pair of electrodes to be used for injecting the IRE and the immobilizing signals. The pair of electrodes may comprise one electrode 30 acting as an injection electrode and another electrode 30 acting as a return electrode. Alternatively the pair may comprise one electrode 30 acting as an injection electrode and external electrode 65 acting as a return electrode. As for the signal parameters, the selection may also be by displaying preset protocols on screen 44, enabling the physician to choose the pair of electrodes to be used for the IRE ablation.

In an insertion step 404, to begin the procedure, physician 22 inserts catheter 26 into subject 24 via a lumen of the subject, and then navigates the catheter, using a control handle 70, so that the selected injected electrode 30 is in proximity to a selected portion of tissue 58, herein termed the target tissue, to be ablated. Processor 32 uses tracking module 60 for the navigation. The module typically displays, on an image of heart 52 presented on screen 44, the position of distal end 28 and electrodes 30, including injection electrode 30 selected in step 400.

When the injection electrode has been positioned to be in proximity to the target tissue, physician 22 initiates the IRE ablation by providing a control signal to processor 32 by any convenient means, such as using control handle 70, input devices 42, or a foot switch (not shown).

On receipt of the control signal, processor 32 implements an immobilization step 408 and, consecutively, a concluding ablation step 412.

In immobilization step 408 the processor uses IRE module 34 to produce immobilizing signal 302, configured according to the values selected in setup step 400, and generally as illustrated in FIG. 4. The processor directs the immobilizing signal to injection electrode 30, so that the electrode injects the immobilizing signal into subject 24. The immobilizing signal immobilizes subject 24.

On completion of injection of the immobilizing signal, when subject 24 is immobilized, the processor proceeds to ablation step 412. In step 412 the processor uses IRE module to produce ablation signal 308, also configured according to the values selected in setup step 400, and generally as illustrated in FIG. 4. As for step 408, in step 412 the processor directs the ablation signal to injection electrode 30, so that the electrode injects the ablation signal into subject 24, ablating the target tissue.

As used herein, the terms "about" or "approximately" for any numerical values or ranges of an entity indicate a suitable dimensional tolerance that allows the entity to function for its intended purpose as described herein. More specifically, "about" or "approximately" may refer to the range of values ±20% of the recited value, e.g. "about 90%" may refer to the range of values from 72% to 108%, and "approximately 0.5 s" may refer to the range of values from 0.4 s to 0.6 s.

EXAMPLES

Example 1. A method for ablating tissue (58) in a subject (24), comprising:
providing a probe (26), comprising an electrode (30), configured to be inserted into a lumen of the subject, so that the electrode is in proximity to the tissue to be ablated;
injecting an immobilizing signal into the subject, via the electrode, that is configured to immobilize the subject; and
when the subject is immobilized, injecting an ablation signal via the electrode into the subject, the ablation signal being configured to ablate the tissue of the subject by irreversible electroporation,
wherein the ablation signal comprises at least one train of first pulses, each of the first pulses in the at least one train having a first pulse absolute amplitude, and wherein the immobilizing signal comprises one or more trains of second pulses, each of the second pulses in the one or more trains having a second pulse absolute amplitude less than the first pulse absolute amplitude.

Example 2. The method according to example 1, wherein the immobilizing signal comprises a plurality of trains of the second pulses, and wherein the second pulse absolute amplitude of each of the plurality increases monotonically in time.

Example 3. The method according to example 2, wherein the monotonic increase is linear.

Example 4. The method according to example 2, wherein the monotonic increase is non-linear.

Example 5. The method according to example 1, wherein each train in the at least one train of first pulses and in the one or more trains of second pulses comprises a plurality of pulses.

Example 6. The method according to example 1, wherein the second pulse absolute amplitude is between 20% and 70% of the first pulse absolute amplitude.

Example 7. The method according to example 1, wherein the first pulses and the second pulses comprise bipolar pulses.

Example 8. The method according to example 1, wherein an overall time for the immobilizing signal is within a range of 0.4 s to 0.6 s.

Example 9. The method according to example 1, wherein the probe comprises a further electrode (30) configured to receive the injected ablation signal and the injected immobilizing signal.

Example 10. The method according to example 1, and comprising an external electrode (65), located on skin of the subject, configured to receive the injected ablation signal and the injected immobilizing signal.

Example 11. Apparatus for ablating tissue (58) in a subject (24), comprising:
a probe (26), comprising an electrode (30), configured to be inserted into a lumen of the subject, so that the electrode is in proximity to the tissue to be ablated; and
a processor (32), configured to:
inject an immobilizing signal into the subject, via the electrode, that is configured to immobilize the subject, and
when the subject is immobilized, inject an ablation signal via the electrode into the subject, the ablation signal being configured to ablate the tissue of the subject by irreversible electroporation,
wherein the ablation signal comprises at least one train of first pulses, each of the first pulses in the at least one train having a first pulse absolute amplitude, and wherein the immobilizing signal comprises one or more trains of second pulses, each of the second pulses in the one or more trains having a second pulse absolute amplitude less than the first pulse absolute amplitude.

It will be appreciated that the examples described above are cited by way of example, and that the present disclosure is not limited to what has been particularly shown and described hereinabove. Rather, the scope of the present disclosure includes both combinations and subcombinations of the various features described hereinabove, as well as variations and modifications thereof which would occur to persons skilled in the art upon reading the foregoing description and which are not disclosed in the prior art.

The invention claimed is:

1. A method for ablating tissue in a patient, comprising:
providing a probe, comprising an electrode, configured to be inserted into a lumen of the patient, so that the electrode is in proximity to the tissue to be ablated;
injecting an immobilizing signal into the patient, via the electrode, that is configured to immobilize the patient; and when the patient is immobilized, injecting an ablation signal via the electrode into the patient, the ablation signal being configured to ablate the tissue by irreversible electroporation, wherein the ablation signal comprises at least one train of first pulses, each of the first pulses in the at least one train having a first pulse absolute amplitude, and wherein the immobilizing signal comprises a plurality of trains of second pulses, each of the second pulses in the plurality of trains having a second pulse absolute amplitude below a threshold value to ablate the tissue by irreversible electroporation and wherein the absolute amplitude of the plurality of trains of second pulses increases monotonically in time.

2. The method according to claim 1, wherein the monotonic increase is linear.

3. The method according to claim 1, wherein the monotonic increase is non-linear.

4. The method according to claim 1, wherein each train in the at least one train of first pulses and in the one or more trains of second pulses comprises a plurality of pulses.

5. The method according to claim 1, wherein the second pulse absolute amplitude is between 20% and 70% of the first pulse absolute amplitude.

6. The method according to claim 1, wherein the first pulses and the second pulses comprise bipolar pulses.

7. The method according to claim 1, wherein an overall time for the immobilizing signal is within a range of 0.4 s to 0.6 s.

8. The method according to claim 1, wherein the probe comprises a further electrode configured to receive the injected ablation signal and the injected immobilizing signal.

9. The method according to claim 1, and comprising an external electrode, located on skin of the patient, configured to receive the injected ablation signal and the injected immobilizing signal.

10. Apparatus for ablating tissue in a patient, comprising:
a probe, comprising an electrode, configured to be inserted into a lumen of the patient, so that the electrode is in proximity to the tissue to be ablated; and a processor, configured to:
inject an immobilizing signal into the patient, via the electrode, that is configured to immobilize the patient, and when the patient is immobilized, inject an ablation signal via the electrode into the patient, the ablation signal being configured to ablate the tissue by irreversible electroporation, wherein the ablation signal comprises at least one train of first pulses, each of the first pulses in the at least one train having a first pulse absolute amplitude, and wherein the immobilizing signal comprises a plurality of trains of second pulses, each of the second pulses in the plurality of trains having a second pulse absolute amplitude below a threshold value to ablate the tissue by irreversible electroporation and wherein the absolute amplitude of the plurality of trains of second pulses increases monotonically in time.

11. The apparatus according to claim 10, wherein the monotonic increase is linear.

12. The apparatus according to claim 10, wherein the monotonic increase is non-linear.

13. The apparatus according to claim 10, wherein each train in the at least one train of first pulses and in the one or more trains of second pulses comprises a plurality of pulses.

14. The apparatus according to claim 10, wherein the second pulse absolute amplitude is between 20% and 70% of the first pulse absolute amplitude.

15. The apparatus according to claim 10, wherein the first pulses and the second pulses comprise bipolar pulses.

16. The apparatus according to claim 10, wherein an overall time for the immobilizing signal is within a range of 0.4 s to 0.6 s.

17. The apparatus according to claim 10, wherein the probe comprises a further electrode configured to receive the injected ablation signal and the injected immobilizing signal.

18. The apparatus according to claim 10, and comprising an external electrode, located on skin of the patient, configured to receive the injected ablation signal and the injected immobilizing signal.

* * * * *